United States Patent [19]

McCormack et al.

[11] Patent Number: 5,328,759
[45] Date of Patent: Jul. 12, 1994

[54] PROCESS FOR MAKING A HYDRAULICALLY NEEDLED SUPERABSORBENT COMPOSITE MATERIAL AND ARTICLE THEREOF

[75] Inventors: Ann L. McCormack, Cumming; Fred R. Radwanski, Roswell; Cherie H. Everhart, Alpharetta, all of Ga.

[73] Assignee: Kimberly-Clark Corporation, Neenah, Wis.

[21] Appl. No.: 786,437

[22] Filed: Nov. 1, 1991

[51] Int. Cl.$^5$ ............................................. B32B 5/16
[52] U.S. Cl. .................................... 428/283; 28/104; 28/105; 28/117; 156/308.2; 428/131; 428/137; 428/138; 428/284; 428/287; 428/296; 428/297; 428/248; 428/299; 428/219
[58] Field of Search ............... 428/131, 137, 138, 283, 428/297, 298, 299, 284, 296, 219, 287; 156/73.1, 272.2, 273.3, 308.2, 298, 279; 28/104, 105, 117

[56] References Cited

U.S. PATENT DOCUMENTS

| | | |
|---|---|---|
| 2,862,251 | 12/1958 | Kalwaites ............................ 19/161 |
| 3,498,874 | 3/1970 | Evans et al. ........................ 161/109 |
| 3,686,024 | 8/1972 | Nankee et al. ................... 117/140 A |
| 3,750,237 | 8/1973 | Kalwaites .......................... 19/161 P |
| 4,096,312 | 6/1978 | Holst et al. ........................ 428/297 |
| 4,260,443 | 4/1981 | Lindsay et al. .................... 156/220 |
| 4,392,908 | 7/1983 | Dehnel ............................... 427/194 |
| 4,442,161 | 4/1984 | Kirayoglu et al. ................. 428/219 |
| 4,582,666 | 4/1986 | Kenworthy et al. ............... 264/557 |
| 4,600,462 | 7/1986 | Watt ................................. 156/278 |
| 4,623,575 | 11/1986 | Brooks et al. ..................... 427/113 |
| 4,675,209 | 6/1987 | Pedigrew .......................... 427/194 |
| 4,735,842 | 4/1988 | Buyofsky et al. ................. 428/134 |
| 4,755,421 | 7/1988 | Manning et al. .................. 428/224 |
| 4,775,579 | 10/1988 | Hagy et al. ........................ 428/284 |
| 4,810,568 | 3/1989 | Buyofsky et al. ................. 428/284 |
| 4,851,069 | 7/1989 | Packard et al. .................... 156/284 |
| 4,879,170 | 11/1989 | Radwanski et al. ............... 428/233 |
| 4,883,709 | 11/1989 | Nozaki et al. ..................... 428/288 |
| 4,931,355 | 6/1990 | Radwanski et al. ............... 428/283 |
| 4,939,016 | 7/1990 | Radwanski et al. ............... 428/152 |
| 4,950,531 | 8/1990 | Radwanski et al. ............... 428/284 |
| 5,009,747 | 4/1991 | Viazmensky et al. ............. 162/115 |

FOREIGN PATENT DOCUMENTS

0359615A1  3/1990  European Pat. Off. .
WO90/04066  4/1990  PCT Int'l Appl. .

OTHER PUBLICATIONS

"Aspects of Jetlace Technology as Applied to Wet-Laid Non-Wovens", Nonwovens Conference—Nov. 1987.
"Wipes for Hydroentanglement Systems", Nonwovens Fabrics Forum, Jun. 1988.
"Hydroentanglement Technology Applied to Wet-Formed and Other Precursor Webs", *TAPPI Journal*, Jun. 1990, pp. 187-192.

*Primary Examiner*—James J. Bell
*Attorney, Agent, or Firm*—Karl V. Sidor

[57] ABSTRACT

Disclosed is a process of making an superabsorbent composite material which contains a hydraulically-needled fibrous web and superabsorbent materials. The method includes the steps of providing a nonwoven fibrous web; hydraulically needling the nonwoven web to enhance its liquid distribution properties; and introducing dry superabsorbent materials into intimate bonding contact with at least one surface of the hydraulically needled fibrous web. Also disclosed is the superabsorbent nonwoven composite material made by the described process. The hydraulically needled fibrous web component of the material may contain pulp fibers, synthetic fibers, natural fibers, bicomponent fibers, continuous filaments or mixtures thereof. The superabsorbent composite material has a saturation capacity greater than about 500 percent and a wicking rate greater than about 12 centimeters per 15 minutes. The superabsorbent composite material may be used as a liquid management material in an absorbent product or absorbent structure.

27 Claims, 10 Drawing Sheets

PROCESS FOR MAKING A HYDRAULICALLY NEEDLED SUPERABSORBENT COMPOSITE MATERIAL AND ARTICLE THEREOF

FIELD OF THE INVENTION

The present invention relates to a process of making an absorbent composite material which includes a nonwoven fibrous web and superabsorbent materials and products of that process.

BACKGROUND OF THE INVENTION

Superabsorbent materials are known to be useful in products intended to absorb liquids. These materials are most often found in powder or particulate form and have in the past been incorporated into laminates and/or nonwoven fibrous webs so they would be in a form that is easy to handle in high speed manufacturing processes. These laminates and/or webs are also useful for keeping the powder/particulates fixed in the absorbent structure. For example, U.S. Pat. No. 3,686,024, issued Aug. 22, 1972, to Nankee, et al., describes a water absorbent coated article which contains a fibrous support such as, for example, a fabric or a paper backing and a water insoluble polymer. According to the patent, the coated article is made by impressing the water insoluble polymer upon the substrate while the polymer is in the form of a gel substantially swollen with water. U.S. Pat. No. 4,096,312, issued Jun. 20, 1978, to Holst, et al., describes a hydrophilic support web which has been coated with modified cellulose ether. According to the patent, a hydrophilic web such as a tissue or paper web is wetted with water and then coated with crushed or powdered modified cellulose ether and then dried. The U.S. Pat. No. 4,260,443, issued Apr. 7, 1981, to Lindsay, et al., discloses a laminate of tissue-like materials which are Separated by a layer of liquid absorbing material. According to the patent, a dry liquid absorbing material is applied to a first sheet. A second water permeable sheet is superposed on the first sheet. Water is applied to portions of the second sheet to moisten the liquid absorbing material and cause it to serve as an adhesive which bonds the first and second sheets together.

Latex binders, thermoplastic adhesive resins and thermoplastic adhesive films are also disclosed as useful for attaching absorbent materials to a substrate. For example, U.S. Pat. No. 4,392,908, issued Jul. 12, 1983, to Dehnel, discloses a process for making absorbent articles by attaching water soluble particles to a substrate using a thermoplastic adhesive resin. U.S. Pat. No. 4,600,462, issued Jul. 15, 1986, to Watt, discloses an absorbent web which is made by bonding a nonwoven web with an adhesive material, curing the adhesive material, and then coating the treated web with a solution of a water soluble hydrophilic material and drying the web. U.S. Pat. No. 4,675,209, issued Jun. 23, 1987, to Pedigrew, discloses an absorbent composite in which a melt adhesive film is used to affix absorbent particles to a substrate.

Also disclosed are absorbent composites which are made by depositing dried absorbent particles on to a moistened paper or tissue layer or wet laid fibrous web. For example, U.S. Pat. No. 4,851,069, issued Jul. 25, 1989, to Packard, et al., discloses a laminate of tissues enclosing an intermediate layer of absorbent particles. According to the patent, the absorbent particles are applied to the moistened surface of one of the tissue layers. A second tissue layer is superposed on the first tissue/particle layer and the assembly is then bonded together using heat and pressure. European Patent Publication 0359615-A1, published Mar. 21, 1990, describes a superabsorbent composite structure which is made by depositing dry solid superabsorbents directly on a wet laid web of cellulosic fibers prior to drying the wet laid web.

Although these references describe various absorbent structures, they still fail to address problems associated with distributing liquid throughout a structure containing superabsorbent materials to make efficient use of all the superabsorbent materials. When superabsorbent materials are added to nonwoven webs or incorporated into laminates, they generally appear to reduce the liquid distribution properties of those webs or laminates. Thus, there is still a need for an improved absorbent structure which combines desirable liquid absorption/retention properties with desirable liquid distribution properties.

DEFINITIONS

The term "hydraulically needled superabsorbent composite material" as used herein refers to a composite material which includes a hydraulically needled nonwoven fibrous web and superabsorbent materials. Hydraulically needling a nonwoven fibrous web has been found to improve some fluid distribution properties such as, for example, the vertical wicking rate by 10 percent or more over an identical web which has not been hydraulically needled. The proper combination of hydraulically needled fibrous webs having improved fluid distribution properties and superabsorbent materials can provide superior superabsorbent composites. For example, hydraulically needled superabsorbent composites may have an absorptive capacity greater than about 500 percent and a vertical wicking rate greater than about 12 cm per 15 minutes.

The term "saturation capacity" as used herein refers to the capacity of a material to absorb liquid (i.e., water or aqueous solution) over a measured period of time and is related to the total amount of liquid held by a material at its point of saturation. Saturation capacity is determined by measuring the increase in the weight of a material sample resulting from the absorption of a liquid. The general procedure used to measure the saturation capacity is as follows. A sample is soaked for approximately 5 minutes in synthetic urine (synthetic urine Item No. K-C 399105 available from PPG Industries, a business having offices in Appleton, Wisc.). The sample is placed flat on a horizontal screen and allowed to drip for about 1 minute. The sample is then transferred to a different horizontal screen which forms the top surface of a vacuum chamber. A latex dam is placed over the screen to seal the vacuum chamber. A vacuum of about 0.5 psi is drawn. The latex dam is forced against the screen by the vacuum, providing relatively uniform pressure on the sample to squeeze out excess liquid. After about 5 minutes of vacuum pressure, the saturated sample is removed and weighed. The saturation capacity may be expressed, in percent, as the weight of liquid absorbed divided by the dry weight of the sample as in the following equation:

$$\text{Saturation Capacity} = [(\text{saturated sample weight} - \text{sample weight})/\text{sample weight}] \times 100.$$

The term "vertical wicking rate" as used herein refers to the rate at which water is drawn in the vertical direction by a strip of an absorbent material. The vertical wicking rate was determined for a pre-weighed sample of absorbent material (having a machine direction length of about 12 inches and a cross-machine direction width of about 3 inches) by lowering the end of the sample about 0.25 inches (about 1 cm) into synthetic urine (synthetic urine Item No. K-C 399105 available from PPG Industries). The sample is fixed in a vertical position with one end in the synthetic urine, and the distance the liquid wicks along the machine direction of the sample is measured after an interval of about 15 minutes. The sample is then removed from the solution and weighed to measure the wicking pickup, that is, the amount of liquid absorbed by the sample during the vertical wicking test.

The term "machine direction" as used herein refers to the direction of travel of the forming surface onto which fibers are deposited during formation of an nonwoven web.

The term "cross-machine direction" as used herein refers to the direction which is perpendicular to the machine direction defined above.

The term "pulp" as used herein refers to pulp containing fibers from natural sources such as woody and non-woody plants. Woody plants include, for example, deciduous and coniferous trees. Non-woody plants include, for example, cotton, flax, esparto grass, milkweed, straw, jute hemp, and bagasse.

The term "mechanical softening" as used herein refers to softening imparted to a sheet of material by a mechanical process. Exemplary mechanical processes which may be used to soften a sheet of material include calendering, perforating, aperturing, perf-embossing, embossing, pattern embossing, differential drawing, creping and rollers.

The term "superabsorbent" as used herein refers to absorbent materials capable of absorbing at least 10 grams of aqueous liquid (e.g. water, saline solution or synthetic urine Item No. K-C 399105 available from PPG Industries) per gram of absorbent material while immersed in the liquid for 4 hours and holding the absorbed liquid while under a compression force of up to about 1.5 pounds per square inch.

The term "liquid management material" as used herein refers to a material that is able to distribute and retain sufficient amounts of liquid to be useful as part of an absorbent structure or absorbent product. For example, a liquid management material may be used in an absorbent personal care product.

SUMMARY OF THE INVENTION

The present invention addresses the needs discussed above by providing a process for producing a hydraulically needled superabsorbent composite material. This method includes the steps of providing a nonwoven fibrous web on a foraminous surface; hydraulically needling the nonwoven fibrous web at an energy level sufficient to enhance the liquid distribution properties of the nonwoven web; introducing dry superabsorbent particles onto at least one surface of the hydraulically needled nonwoven fibrous web in intimate bonding contact. According to the invention, the intimate contact between the superabsorbent material and the hydraulically needled fibrous web may be provided by depositing dry superabsorbent material onto the still wet hydraulically needled fibrous web and then and drying the resulting hydraulically needled superabsorbent composite material. In one embodiment of the invention, the intimate bonding contact may be provided by depositing dry superabsorbent material onto a dry hydraulically needled fibrous web and then using mechanical means to drive the superabsorbent material into the hydraulically needled fibrous web.

In one aspect of the invention, the step of providing a nonwoven fibrous web may encompass the step of rehydrating a sheet which includes pulp fibers until it is brought to a consistency suitable for hydraulic needling.

The nonwoven fibrous web may be provided by depositing an aqueous slurry of fibers onto a foraminous surface via conventional wet-laying or papermaking techniques. Such a nonwoven fibrous web may be formed and hydraulically needled on the same foraminous surface. The foraminous surface may be, for example, a single plane mesh having a mesh size of from about 20 ×20 to about 200×200. The foraminous surface may also be a multi-ply mesh having a mesh size from about 20×20 to about 200 ×200. In one embodiment of the present invention the foraminous surface may have a series of ridges and channels and protruding knuckles which impart certain characteristics to the nonwoven web.

According to the present invention, hydraulic needling is provided by jets of a liquid (e.g., water or similar working fluid) which produces a desired loosening and rearrangement of the fiber network in the nonwoven fibrous web. For example, it has been found that when jets of water are used to impart a total energy of less than about 0.03 horsepower-hours/pound of web to a predominantly pulp fiber web, the liquid handling properties of the nonwoven web are improved when compared to an identical sheet which has not been hydraulically needled. The energy imparted by the working fluid for such a pulp fiber web may be between about 0.001 to about 0.03 horsepower-hours/pound of web. Greater amounts of energy may be required for webs containing large proportions of staple-length textile fibers or very high basis weights. Needling typically takes place while the fibrous web is from about 15 to about 35 percent, by weight, solids.

Substantially dry superabsorbent material is deposited onto at least one surface of the wet hydraulically needled nonwoven fibrous web. This superabsorbent material is deposited at a rate which provides a composite that contains at least about 5 percent, by weight, superabsorbent based on the total weight of the substantially dry composite material. For example, the composite may contain from about 10 to about 80 percent, by weight, of superabsorbent materials. Desirably, the composite may contain from about 25 to about 65 percent, by weight, of superabsorbent materials. The superabsorbent materials may be superabsorbent particles, superabsorbent fibers or mixtures thereof. Superabsorbent particles may be deposited on the web utilizing conventional particle spreading equipment. Superabsorbent fibers may be deposited on the web utilizing conventional means for depositing a layer of fibers.

In another aspect of the method of the present invention, the hydraulically needled superabsorbent composite material is dried to a moisture content of less than about 10 percent, by weight. For example, the composite material may be dried to a moisture content of less than about 5 percent. Drying may be achieved using a non-compressive drying process. Through-air drying processes have been found to work particularly well. Other drying processes which incorporate infra-red radiation, yankee dryers, drying cans, microwaves, and ultrasonic energy may also be used.

The present invention also encompasses a hydraulically needled superabsorbent composite material made by the process described above. Certain fibrous webs hydraulically needled to enhance their fluid distribution properties can be combined with superabsorbent materials to produce superior superabsorbent composites which are very inexpensive and have highly desirable liquid distribution and retention properties. Hydraulically needled superabsorbent composite materials made according to the present invention may have a saturation capacity greater than about 500 percent and a vertical wicking rate greater than about 12 cm per 15 minutes. For example, superabsorbent composite materials made according to the present invention may have a saturation capacity between about 600 and about 2500 percent and a vertical wicking rate between about 14 to about 25 cm per 15 minutes. Desirably, the hydraulically needled superabsorbent composite materials may have a saturation capacity between about 800 and about 2000 percent and a vertical wicking rate between about 15 to about 19 cm per 15 minutes. In one exemplary embodiment, the hydraulically needled superabsorbent composite material may have a saturation capacity between about 900 and about 1500 percent and a vertical wicking rate between about 16 to about 18 cm per 15 minutes.

The fibrous component of the superabsorbent composite material may be pulp fibers, synthetic fibers, natural fibers, bicomponent fibers, continuous filaments or mixtures thereof. For example, the hydraulically needled superabsorbent composite material may contain from about 5 to about 50 percent, by weight, staple-length fibers. These staple-length fibers may be staple fibers made from rayon, cotton, polyester, polyamides and polyolefins such as, for example, one or more of polyethylene, polypropylene, polybutene, ethylene copolymers, propylene copolymers and butene copolymers. The staple-length fibers may have a denier in the range of about 0.7 to about 8 and an average length in the range of about 5 mm to about 36 mm.

The present invention also contemplates treating the hydraulically needled superabsorbent composite material with additives such as, for example, binders, surfactants, cross-linking agents, hydrating agents and/or pigments to impart desirable properties such as, for example, abrasion resistance, toughness, color, or improved wetting ability.

One or more layers of the hydraulically needled superabsorbent composite material may be used as a liquid management material in an absorbent product or absorbent structure. In such applications, the hydraulically needled superabsorbent composite material may have a basis weight greater than about 10 grams per square meter. For example, the hydraulically needled superabsorbent composite material may have a basis weight from about 60 to about 400 grams per square meter. The hydraulically needled superabsorbent composite material may be used as a liquid management material in applications such as, for example, disposable personal care products, food and product packaging, wipers, wound dressings, medical absorbent products, industrial sorbents, kennel and catbox liners.

DETAILED DESCRIPTION OF THE INVENTION

Figure 1:
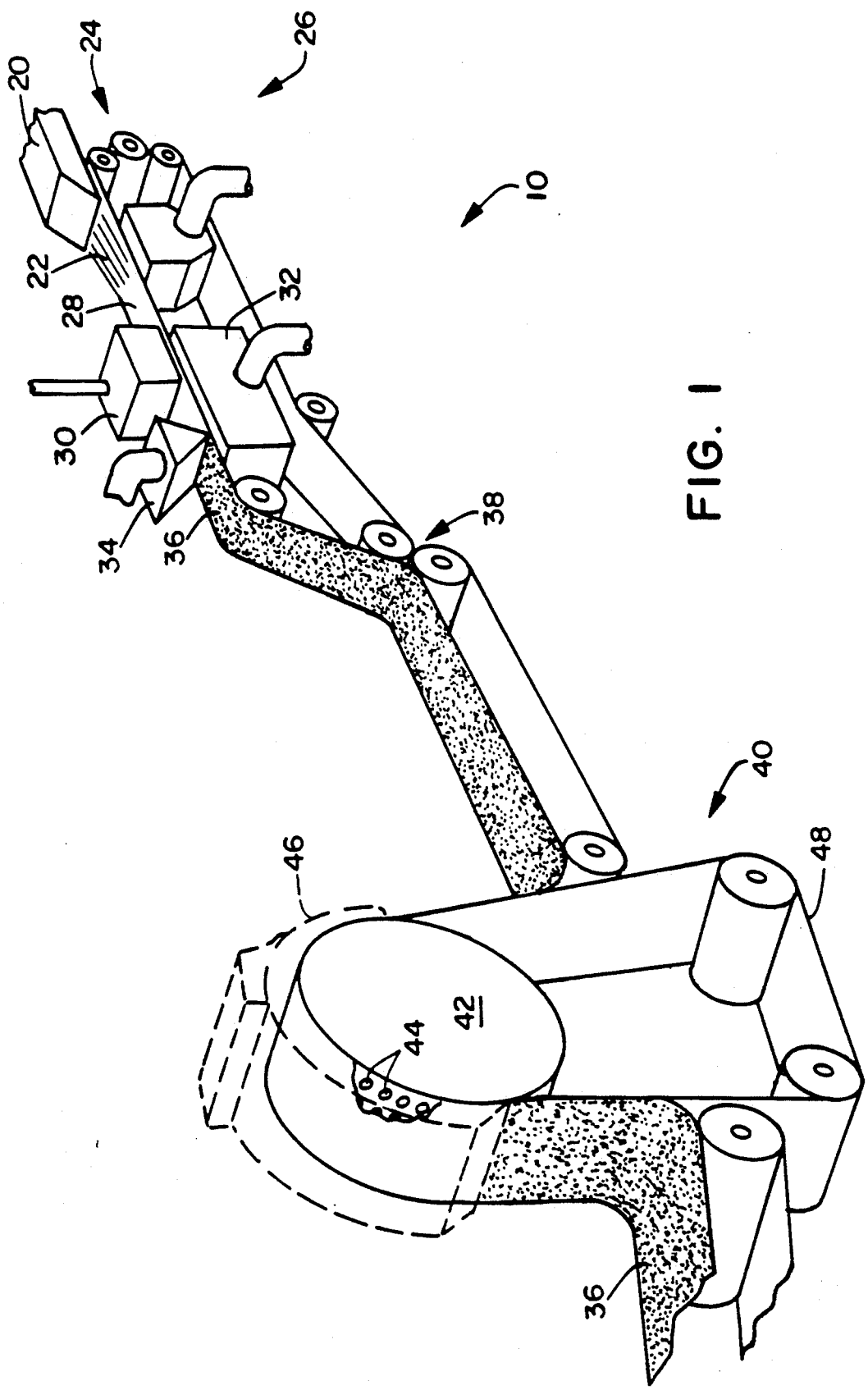
FIG. 1 is an illustration of an exemplary process for making a hydraulically needled superabsorbent composite material which includes a fibrous nonwoven web and superabsorbent materials.

Referring to FIG. 1 of the drawings there is schematically illustrated at 10 a process for forming a hydraulically needled superabsorbent composite material. This composite includes a hydraulically needled nonwoven fibrous web and superabsorbent materials. The nonwoven fibrous web may be made by forming a dilute suspension of fibers, supplying that suspension to a headbox 20 and depositing it via a sluice 22 as a uniform dispersion onto a foraminous screen 24 of a conventional papermaking machine 26. The suspension of fibers may be diluted to any consistency which is typically used in conventional wet-laying processes. For example, the suspension may contain from about 0.02 to about 5 percent by weight fibers suspended in water.

The fibers may be pulp fibers from woody or nonwoody plants as well as secondary (i.e., recycled) fiber pulp. Exemplary wood pulps include bleached and unbleached kraft virgin softwood fiber pulps and bleached and unbleached kraft virgin hardwood pulp. Some useful pulps are those available from the Kimberly-Clark Corporation under the trade designations Longlac 19, Longlac 16, Coosa River 55, Coosa River 56, and Coosa River 57. Secondary fiber pulp may be pulp fibers recycled from sources such as, for example, office waste, newsprint, and paperboard scrap. For example, one useful secondary fiber pulp identified as "BJ deinked secondary fiber pulp" is available from Ponderosa Pulp Products—a division of Ponderosa Fibers of America, Atlanta, Ga.

The pulp fibers may be unrefined or may be beaten to various degrees of refinement. Small amounts of wet-strength resins and/or resin binders may be added to improve strength and 35 abrasion resistance. Useful binders and wet-strength resins include, for example, Kymene ® 557 H available from the Hercules Chemical Company, and Parez 631 available from American Cyanamid, Inc. Cross-linking agents and/or hydrating agents may also be added to the pulp mixture. Debonding agents may be added to the pulp mixture to reduce the degree of hydrogen bonding if a very open or loose (e.g., softer) nonwoven pulp fiber web is desired. One exemplary debonding agent is available from the Quaker Chemical Company, Conshohocken, Penna., under the trade designation Quaker 2008.

The fibers may also be synthetic fibers, natural fibers, bicomponent fibers, or continuous filaments having various deniers and lengths. Mixtures of pulp fibers and these other types of fibers may also be used. For example, the fibrous component of the hydraulically needled superabsorbent composite materials may contain from about 5 to about 50 percent, by weight, staple length fibers and from about 50 to 95 percent, by weight pulp fibers.

The synthetic fibers may be made from rayon, polyester, polyamides and polyolefins such as, for example, one or more of polyethylene, polypropylene, polybutene, ethylene copolymers, propylene copolymers and butene copolymers. Natural fibers may include, for example, cotton, cotton linters, wool, silk, and flax. Typically, these fibers will have a denier in the range of about 0.7 to about 8 and an average length in the range of about 5 mm to about 36 mm. For example, the fibers may have a denier in the range of about 0.9 to about 3 and an average length in the range of about 10 mm to about 24 mm. Desirably, the fibers may have a denier in the range of about 1 to about 2 and an average length in the range of about 12 mm to about 18 mm.

The suspension of fibers is deposited on the foraminous surface 24 and water is removed to form a uniform nonwoven web of fibers 28. Hydraulic needling may take place on the foraminous surface (i.e., mesh fabric) 24 on which the wet-laid web is formed. Alternatively, the web may be transferred to a different foraminous surface for hydraulic needling. The present invention also contemplates rehydrating a dried fibrous web to a specified consistency and subjecting the rehydrated fibrous web to hydraulic needling. For example, this fibrous web may be a web of pulp fibers or a web containing a mixture of pulp fibers and other fibers.

The nonwoven web 28 passes under one or more hydraulic needling manifolds 30 and is treated with jets of fluid to open up or loosen and rearrange the tight network of fibers. Typically, the hydraulic needling takes place while the nonwoven web is at a consistency between about 15 to about 45 percent solids. For example, the nonwoven web may be at a consistency from about 20 to about 30 percent solids.

According to the invention, the nonwoven fibrous web 28 is hydraulically needled. That is, conventional hydraulic entangling equipment may be operated at conditions which impart relatively low energies (e.g., 0.001 to 0.03 hp-hr/lb) to the web. Water jet treatment equipment which may be adapted to the process of the present invention may be found, for example, in U.S. Pat. No. 3,485,706 to Evans, the disclosure of which is hereby incorporated by reference. The hydraulic needling process of the present invention may be carried out with any appropriate working fluid such as, for example, water. The working fluid flows through a manifold which evenly distributes the fluid to a series of individual holes or orifices. These holes or orifices may be from about 0.003 to about 0.015 inch in diameter. For example, the invention may be practiced utilizing a manifold produced by Honeycomb Systems Incorporated of Biddeford, Maine, containing a strip having 0.007 inch diameter orifices, 30 holes per inch and 1 row of holes Many other manifold configurations and combinations may be used. For example, a single manifold may be used or several manifolds may be arranged in succession.

In the hydraulic needling process, the working fluid passes through the orifices at a pressures ranging from about 50 to about 1500 pounds per square inch gage (psig) to form fluid streams which impact the nonwoven fibrous web 28, typically with much less energy than found in conventional hydraulic entangling processes. For example, the working fluid passes through the orifices at a pressures ranging from about 50 to about 800 pounds per square inch gage (psig). Desirably, the working fluid passes through the orifices at a pressures ranging from about 75 to about 400 pounds per square inch gage (psig) for fibrous webs containing a predominance of pulp fibers. More entangling energy may be required for high basis weight materials, nonwoven fibrous webs containing large proportions of staple length fibers, or fibers having a stiffer modulus.

The energy imparted to the nonwoven web by the hydraulic needling process may be expressed in units of horsepower-hours per pound of dry web (hp-hr/lb) and may be calculated utilizing the following equation:

$$Energy = [0.125((Y*P*Q/(S,B))]*N$$

where:
Y = number of orifices per linear inch of manifold;
P = pressure of the water in the manifold expressed in pounds per square inch gauge (psig);
Q = volumetric flow rate of water expressed in cubic feet per minute per orifice;
S = speed of conveyor passing the web under the water jet streams expressed in feet per minute;
B = weight of pulp fibers treated expressed in ounces per square yard;
N = number of manifold passes.

This energy equation may be found in U.S. Pat. No. 3,485,706, previously incorporated herein by reference, which discusses the transfer of energy from columnar fluid jet streams to a nonwoven fibrous web.

Generally speaking, nonwoven fibrous webs that contain mostly pulp fibers may utilize a fluid pressure ranging from about 60 to about 400 psig, when 1 to 4 manifolds are used. As is typical in many water jet treatment processes, vacuum slots 32 may be located directly beneath the hydro-needling manifolds or beneath the foraminous surface 24 downstream of the entangling manifold so that excess water is withdrawn from the hydraulically-needled nonwoven fibrous web 28.

Conventional superabsorbents are deposited on at least one surface of the hydraulically needled nonwoven fibrous web after the water-jet treatments. These superabsorbent materials may be in the form of superabsorbent particles or superabsorbent fibers.

The superabsorbent material may be formed from an organic material such as, for example, agar, pectin, and guar gum, as well as synthetic materials such as synthetic hydrogel polymers. Synthetic hydrogel polymers include, for example, carboxymethylcellulose, alkali metal salts of polyacrylic acid, polyacrylamides, polyvinyl alcohol, ethylene maleic anhydride copolymers, polyvinyl ethers, hydroxypropylcellulose, polyvinyl morpholinone, polymers and copolymers of vinyl sulfonic acid, polyacrylates, polyacrylamides, polyvinyl pyridine, and the like. Other suitable polymers include hydrolyzed acrylonitrile grafted starch, acrylic acid grafted starch, and isobutylene maleic anhydride copolymers and mixtures thereof. The hydrogel polymers are preferably lightly crosslinked to render the material substantially water-insoluble. Crosslinking may, for example, be by irradiation or by covalent, ionic, Van der Waals, or hydrogen bonding. Suitable materials are available from various commercial vendors, such as the Dow Chemical Company, Hoechst Celanese Corporation, Allied-Colloid Inc., and Stockhausen Inc. For example, useful sodium polyacrylate superabsorbent particles are available from the Hoechst Celanese Corporation under the trade name Sanwet IM-5000 P.

Superabsorbent particles and/or fibers are added to the hydraulically needled nonwoven fibrous web by a conventional particulate and/or fiber handling system 34 to form the hydraulically needled superabsorbent composite material 36. It is contemplated that the hydraulically needled nonwoven fibrous web may be either wet or dry during this step. Exemplary particulate handling systems are described in, for example, U.S. Pat. No. 4,604,313, the contents of which regarding particulate handling systems is incorporated herein by reference. Useful particulate handling systems include various engraved roll volumetric feeders as well as other commercial systems such as, for example, Christy dry material dispensing machines available from the Christy Machine Company of Fremont, Ohio; and Meltex ™ SAP series powder application systems available from the Nordson Corporation. Useful fiber handling systems include staple fiber web air-forming systems as well as commercial systems available from Moller & Jochumsen of Denmark and Danweb Forming International.

Superabsorbents may be present at a proportion of up to about 80 grams of superabsorbent per 100 grams total weight of the substantially dry composite material. For example, the nonwoven web may contain from about 15 to about 65 grams of superabsorbent per 100 grams total weight of the substantially dry composite material. More particularly, the nonwoven web may contain about 40 to about 50 grams of superabsorbent per 100 grams total weight of the substantially dry composite material.

It is contemplated that superabsorbent materials may be deposited on the nonwoven fibrous web prior to the fluid jet treatments. If superabsorbent materials are deposited on the wet-laid web before water-jet treatments, it is preferred that the superabsorbents are those which can remain inactive during the water-jet treatment step and can be activated later.

After the superabsorbent materials are added, the hydraulically needled superabsorbent composite material 36 is transferred to a drying operation. A differential speed pickup roll 38 may be used to transfer the web from the hydraulic needling belt to the drying operation. Alternatively, conventional vacuum-type pickups and transfer fabrics may be used. Desirably, the drying operation is a non-compressive drying operation. For example, the web may be non-compressibly dried utilizing a conventional rotary drum through-air drying apparatus shown in FIG. 1 at 40. The through-dryer 40 may be an outer rotatable cylinder 42 with perforations 44 in combination with an outer hood 46 for receiving hot air blown through the perforations 44. A through-dryer belt 48 carries the composite 36 over the upper portion of the through-dryer outer cylinder 42. The heated air forced through the perforations 44 in the outer cylinder 42 of the through-dryer 40 removes water from the composite 36. The temperature of the air forced through the composite 36 by the through-dryer 40 may range from about 300° to about 500° F. Other useful through-drying methods and apparatus may be found in, for example, U.S. Pat. Nos. 2,666,369 and 3,821,068, the contents of which are incorporated herein by reference.

It may be desirable to use finishing steps and/or post-treatment processes to impart selected properties to the composite 36. For example, the web may be mechanically softened. This softening may be accomplished by calendering, perforating, aperturing, perf-embossing, embossing, pattern embossing, differential drawing, creping, and rollers. Softening may also be accomplished by adding debonding agents to the nonwoven fibrous web before or just after the hydraulic needling step. Alternatively and/or additionally, chemical post-treatments may be added to the web such as, for example, adhesives, dyes, surfactants, cross-linking agents, hydrating agents and/or pigments to impart desirable properties such as, for example, abrasion resistance, toughness, color, or improved wetting ability.

Figure 2:
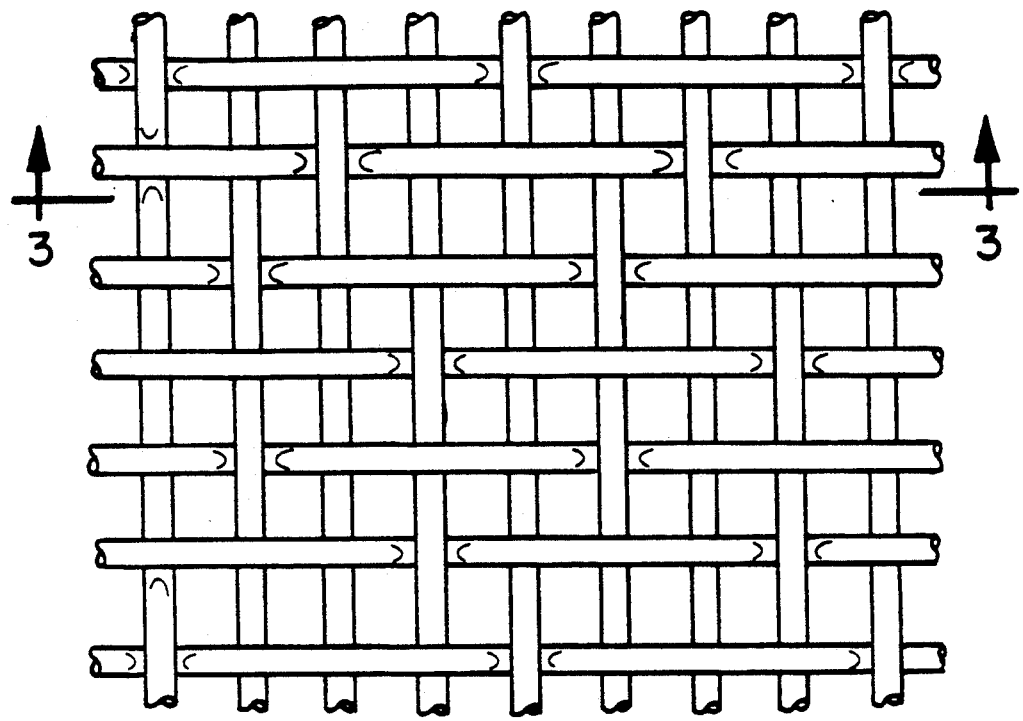
FIG. 2 is a view of the top of an exemplary multi-ply mesh fabric suitable as a supporting surface for hydraulic needling of a nonwoven fiber web.
Figure 3:
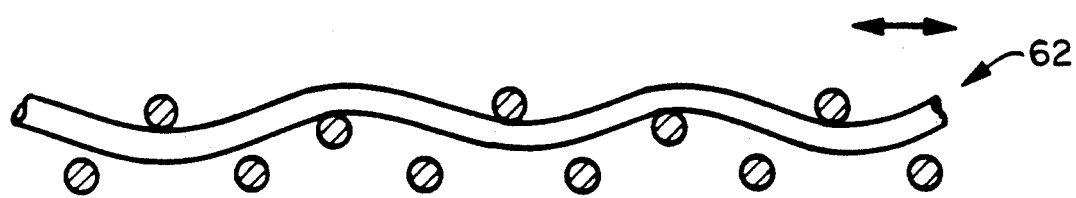
FIG. 3 is a sectional view taken along 3—3 of FIG. 2 showing one ply of an exemplary multi-ply mesh fabric.
Figure 4:
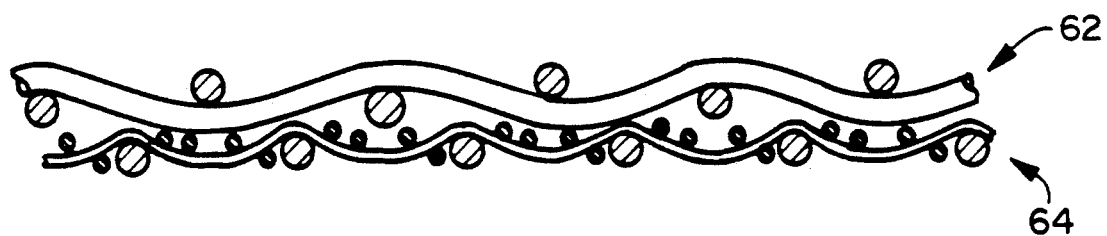
FIG. 4 is a sectional view taken on 3—3 of FIG. 2 showing two plies of an exemplary multi-ply mesh fabric.

FIG. 2 is a view of the top ply of an exemplary multi-ply mesh fabric used in making the absorbent nonwoven composite material of the present invention. In FIG. 2, line 3—3 runs across the multi-ply mesh fabric in the cross-machine direction. The multi-ply (i.e., compound) fabric may include a coarse layer joined to fine layer. FIG. 3 illustrates a sectional view taken along line 3—3 of a coarse layer 62 (a simple single layer weave) of the exemplary mesh fabric. FIG. 4 illustrates a sectional view taken along 3—3 of a coarse layer 62 joined to a fine layer 64 (another simple single layer weave). Preferably, the coarse layer 62 has a mesh (i.e., warp yarns of fabric per inch of width) of about 50 or less and a count (shute yarns of fabric per inch of length) of about 50 or less. For example, the coarse layer 62 may have a mesh of about 35 to 40 and a count of about 35 to 40. More particularly, the coarse layer 62 may have a mesh of about 38 and a count of about 38. The fine layer 64 preferably has a mesh and count about twice as great as the coarse layer 62. For example, the fine layer 64 may have a mesh of about 70 to about 100 and a count of about 70 to about 100. In particular, the fine layer 64 may have a mesh of about 70 to 80 and a count of about 70 to 80. More particularly, the fine layer may have a mesh of about 75 and a count of about 75.

Figure 5:
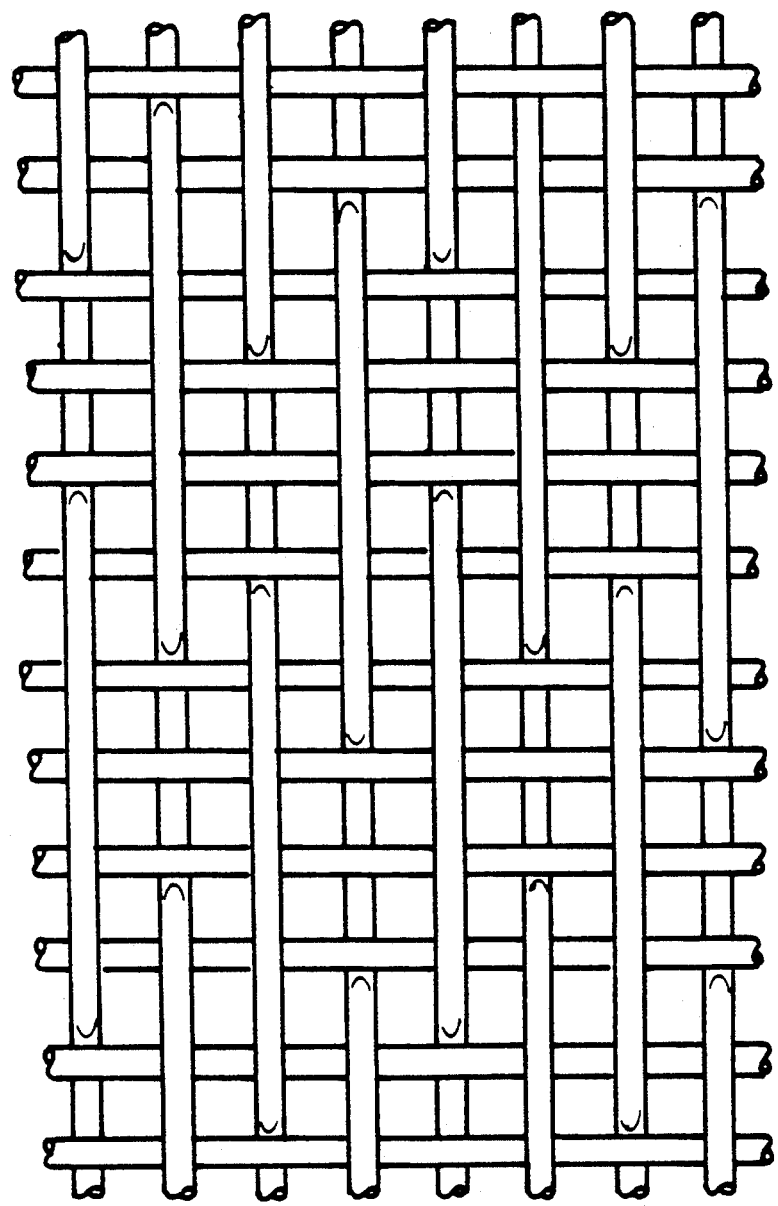
FIG. 5 is a bottom view of one ply of an exemplary multi-ply mesh fabric.
Figure 6:
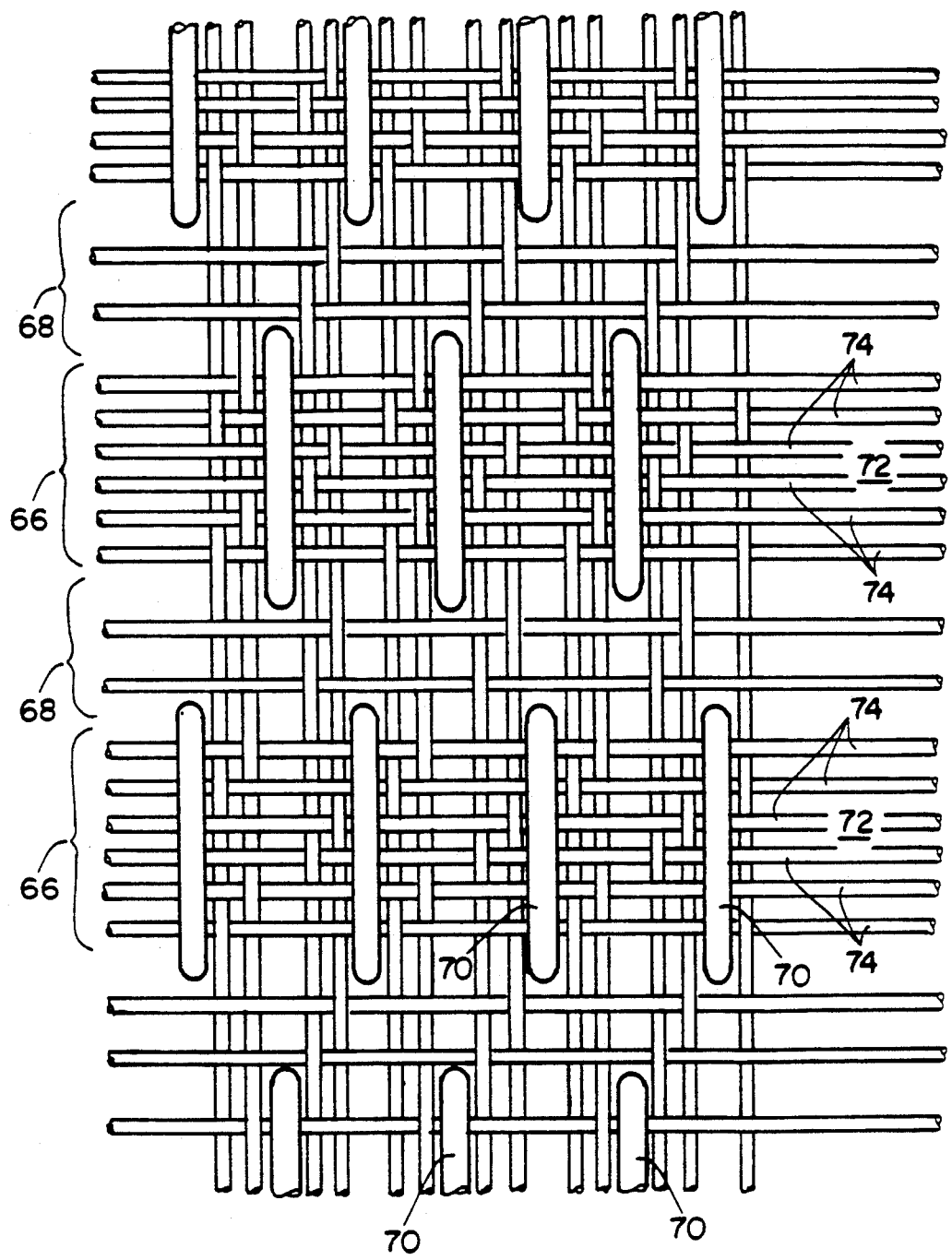
FIG. 6 is a bottom view of an exemplary multi-ply mesh fabric showing two plies of the fabric.

FIG. 5 is a bottom view of the coarse layer without the fine layer. FIG. 6 is a bottom view of the multi-ply mesh fabric showing the coarse layer interwoven with the fine layer illustrating a preferred weave construction. The particular weave provides cross-machine direction channels defining high drainage zones 68 which are separated by low drainage zones 66. The warp strands 70 of the coarse layer are arranged in rows 72 which define channels that run along the top of the fabric in the cross-machine direction. These warp strands 70 are woven to gather groups of filaments 74 (also running in cross-machine direction) of the fine layer. The rows 72 of warp strands 70 are matched with the groups of filament 74 to provide the low drainage zones 66 which separate the high drainage zones 68.

During the fluid-jet treatments, the fibrous web generally conforms to the topography of the coarse layer to provide a textile-like appearance. Flow of fluid through the fabric is controlled by the high drainage zones and the fine layer on the bottom of the fabric to provide the proper conditions for loosening/opening the pulp fiber network during hydraulic needling while avoiding web break-up, washout of short fibers and intertwining of fibers into the mesh fabric. In some embodiments, the weave patterns may have certain filaments (e.g., warp strands) which protrude to form knuckles. Fibers may be washed off portions of these knuckles to form small pores or apertures.

The present invention may be practiced with other fabrics. In general, the fabric must be fine enough to avoid fiber washout and yet allow adequate drainage. For example, the nonwoven web may be wet laid and hydraulically needled on a conventional single plane mesh having a mesh size ranging from about 20×20 to about 200×200 (expressed as filaments per inch in the machine direction and filaments per inch in the cross-machine direction). The fabric may also be a multi-ply mesh having a mesh size from about 20×20 to about 200×200. Such a multi-ply mesh may be particularly useful when secondary fibers are incorporated into the nonwoven web. Useful fabrics include, for example, Asten-856, Asten 892, and Asten Synweve Design 274, fabrics available from Asten Forming Fabrics, Inc. of Appleton, Wisc., and conventional 55×38 mesh and 100×92 mesh stainless steel semi-twill fabrics available from National Wire Fabric of Star City, Ark. In some situations, it may be desirable to perform the hydraulic needling on perforated plates instead of a conventional fabric.

Generally speaking, forming fabrics which are closed and flat provide an adequate surface for forming and needling the fibrous nonwoven web. The resulting web has few, if any, large holes which would allow superabsorbent materials to be vacuumed through the web and into the forming fabric.

Figure 7:
FIG. 7 is a 30.5× photomicrograph of a cross section of an exemplary wet-laid pulp fiber web which has not been hydraulically needled and which contains no superabsorbent.

FIG. 7 is a 30.5× photomicrograph of a cross section of an exemplary wet-laid pulp fiber web which has not been hydraulically needled and which contains no superabsorbent. This is the material from Example 5A which has a basis weight of about 78 grams per square meter.

Figure 8:
FIG. 8 is a 30.5× photomicrograph of a cross section of an exemplary hydraulically needled pulp fiber web which contains no superabsorbent.

FIG. 8 is a 30.5× photomicrograph of a cross section of an exemplary hydraulically needled pulp fiber web which has a basis weight of about 78 grams per square meter. This is the material from Example 5B which was needled on a conventional 100×92 mesh stainless steel semi-twill wire moving at about 25 ft/min at a pressure of about 200 psi from 3 manifolds each equipped with a jet strip having 0.007 inch diameter holes (1 row of holes at a density of 30 holes per inch).

Figure 9:
FIG. 9 is a 61× photomicrograph of a cross section of an exemplary wet-laid pulp fiber web which has not been hydraulically needled and which contains no superabsorbent.

FIG. 9 is a 61× photomicrograph of a cross section of the material shown in FIG. 7.

Figure 10:
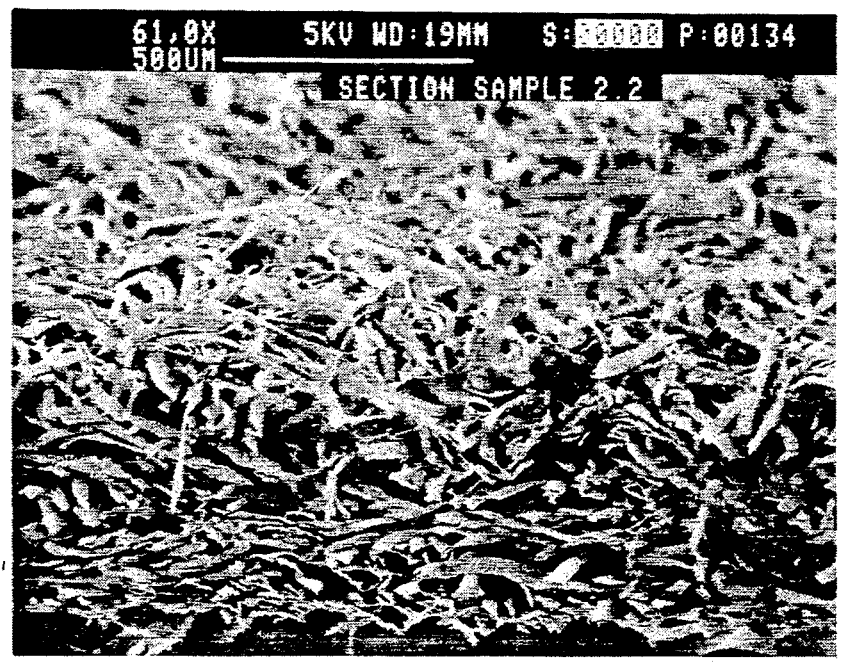
FIG. 10 is a 61× photomicrograph of a cross section of an exemplary hydraulically needled pulp fiber web which contains no superabsorbent.

FIG. 10 is a 61× photomicrograph of a cross section of the material shown in FIG. 8.

Figure 11:
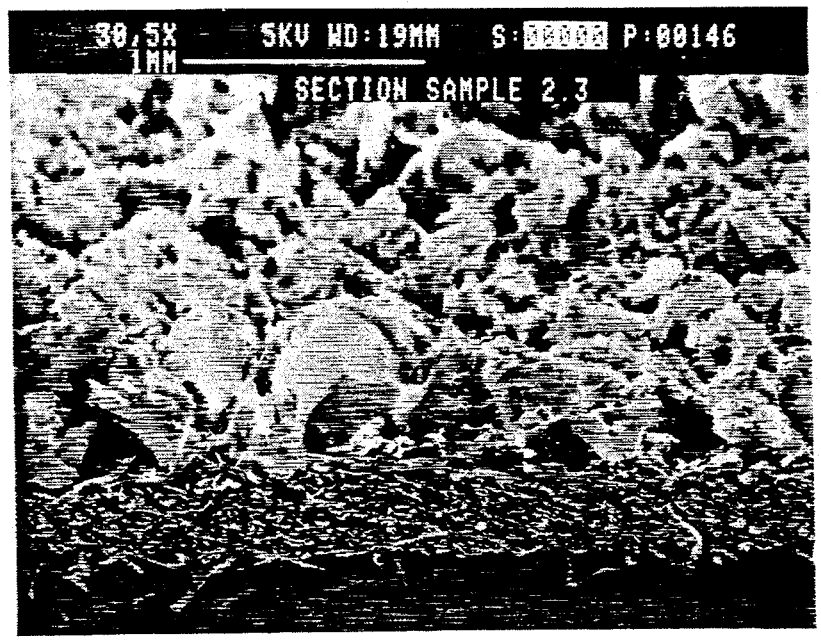
FIG. 11 is a 30.5× photomicrograph of a cross section of an exemplary composite which contains superabsorbent materials deposited on a wet-laid pulp fiber web that has not been hydraulically needled.

FIG. 11 is a 30.5× photomicrograph of a cross section of an exemplary composite containing superabsorbent materials deposited on a wet-laid pulp fiber web that has not been hydraulically needled. This is the material from Example 6A which has a basis weight of about 185 grams per square meter and contains about 60% by weight superabsorbent.

Figure 12:
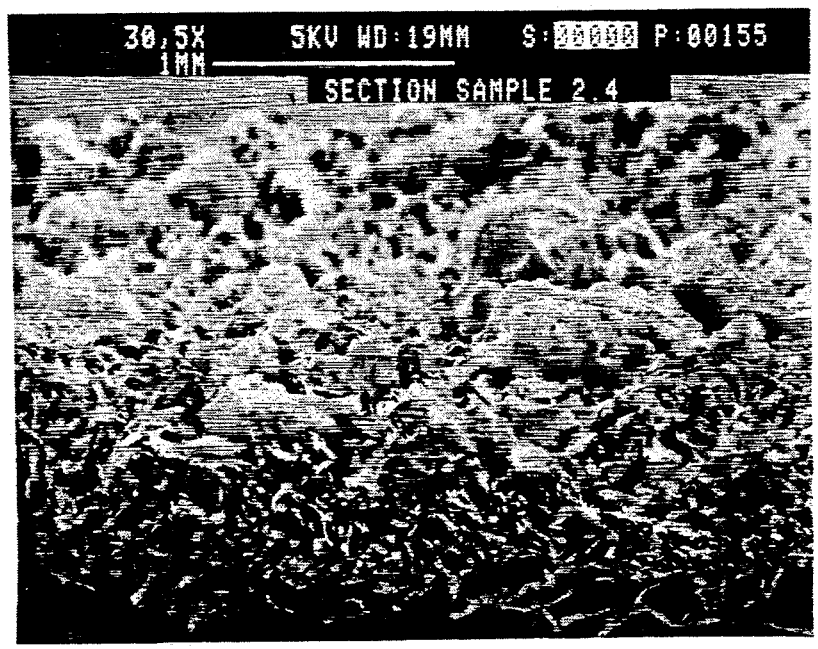
FIG. 12 is a 30.5× photomicrograph of a cross section of an exemplary hydraulically needled superabsorbent composite material.

FIG. 12 is a 30.5× photomicrograph of a cross section of an exemplary hydraulically needled superabsorbent composite material. This is the material from Example 6B which has a basis weight of about 150 grams per square meter, contains about 50% by weight superabsorbent and was needled on a conventional 100×92 mesh stainless steel semi-twill wire moving at about 25 ft/min at a pressure of about 200 psi from 3 manifolds each equipped with a jet strip having 0.007 inch diameter holes (1 row of holes at a density of 30 holes per inch).

Figure 13:
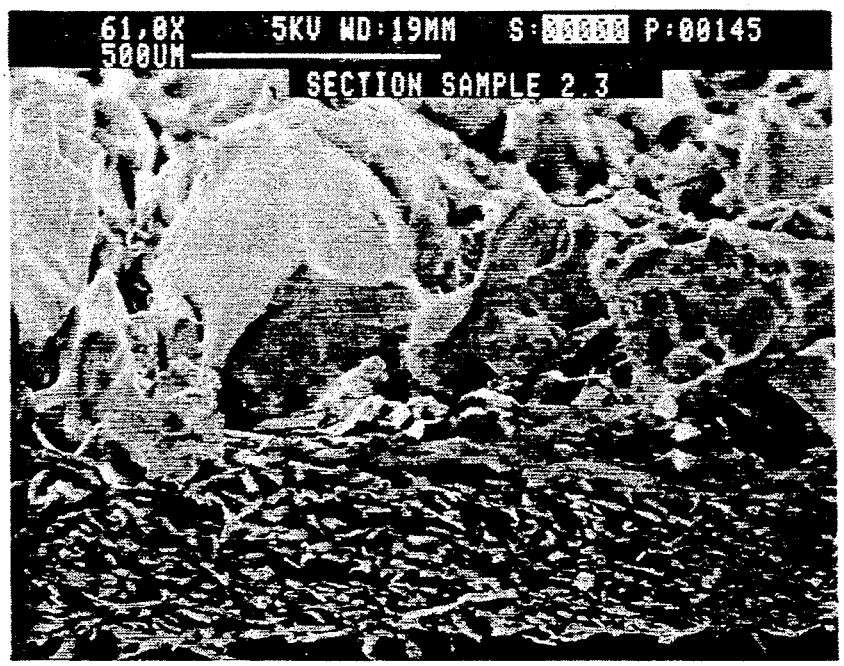
FIG. 13 is a 61× photomicrograph of a cross section of an exemplary composite which contains superabsorbent materials deposited on a wet-laid pulp fiber web that has not been hydraulically needled.

FIG. 13 is a 61× photomicrograph of a cross section of the material shown in FIG. 11.

Figure 14:
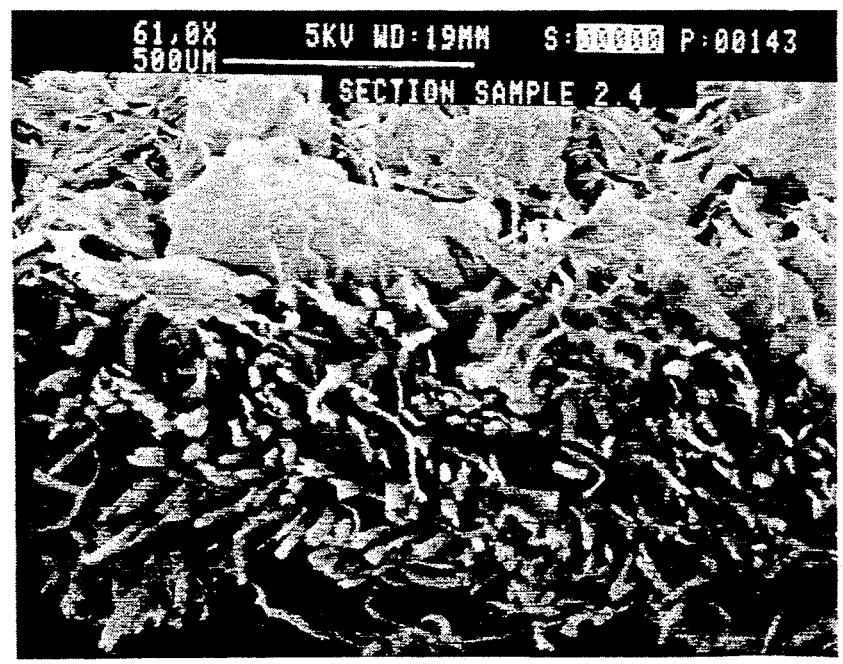
FIG. 14 is a 61× photomicrograph of a cross section of an exemplary hydraulically needled superabsorbent composite material.

FIG. 14 is a 61× photomicrograph of a cross section of the material shown in FIG. 12.

When comparing the hydraulically needled fibrous webs (FIGS. 8 and 10) with their untreated counterparts (FIGS. 7 and 9), the hydraulically needled fibrous webs have a relatively loose fiber structure and also appear to have many fibers with a Z-direction orientation. Such an open and loose fiber network appears to improve the saturation capacity and vertical wicking properties of the fibrous web.

A comparison of the hydraulically needled superabsorbent composite materials (FIGS. 12 and 14) with their untreated counterparts (FIGS. 11 and 13), reveals that the hydraulically needled superabsorbent composite materials provide a much more intimate contact between the superabsorbent particles and the fibrous web. Instead of point contacts, there appears to be higher area contact between the two types of materials. The larger interface improves the transfer of liquid from the fibrous material to the superabsorbent particles.

Although the inventors should not be held to a particular theory of operation, it is believed that the columnar jets of working fluid which directly impact fibers laying in the X-Y plane of nonwoven web work to rearrange some of those fibers into the Z-direction. The jets of working fluid also wash some fibers off knuckles, ridges or raised portions of the foraminous surface. This washing action appears to create pores and/or apertures on the raised portions or knuckles of the foraminous surface. This uneven topography and the presence of pores and/or apertures in the hydraulically needled fibrous web provide enclosures which partially surround the absorbent particles to help improve contact with the particles and to help the fibrous webs hold onto the particles.

Desirably, improved contact is provided by depositing dry superabsorbent materials onto the hydraulically needled fibrous web while the web is still wet. It is also contemplated that improved contact can be provided by depositing dry superabsorbent materials onto a relatively dry hydraulically needled fibrous web and then using mechanical means such as, for example, rollers, to drive the superabsorbent materials into the hydraulically needled fibrous web. A second hydraulically needled fibrous web may also be superposed on the composite and joined by point bonding to create a superabsorbent laminate.

The jets of working fluid also appear to create deposits of fibers which correspond to channel-like portions of the foraminous surface and which appear to serve as relatively continuous conduits extending in the X-Y direction which help to transport liquid in that direction. Additionally, the Z-direction oriented fibers are believed to enhance the transfer of liquid from these relatively continuous conduits to the superabsorbent particles. As the superabsorbent particles absorb liquid, they are believed to help draw liquid along those relatively continuous conduits.

When carefully controlled, the results of the direct impact and washing action of the jets, in combination with the superabsorbent particles increase certain desirable liquid distribution and absorbency characteristics (e.g., saturation capacity and wicking rate) of the nonwoven fibrous web.

Figure 15:
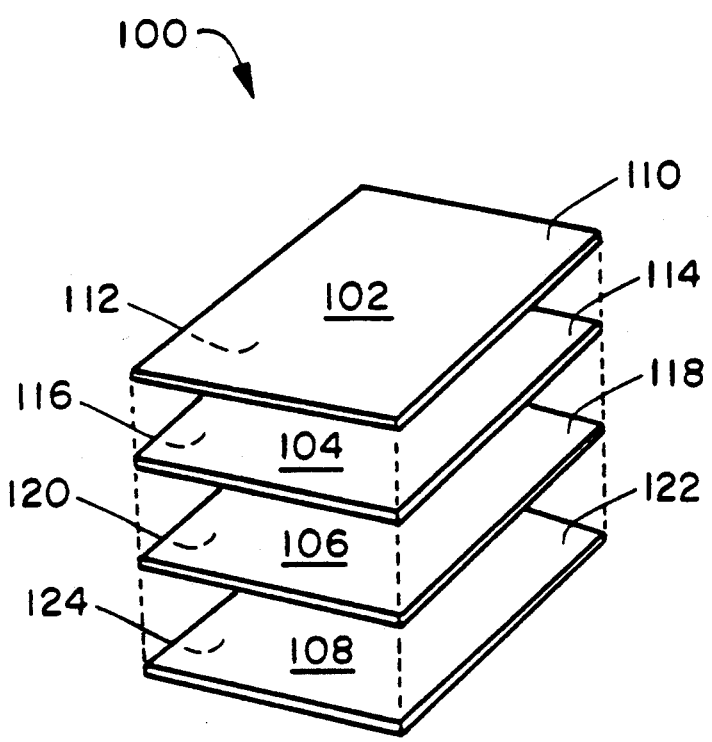
FIG. 15 is a representation of an exemplary absorbent structure that contains a hydraulically needled superabsorbent composite material.

FIG. 15 is an exploded perspective view of an exemplary absorbent structure 100 which incorporates a hydraulically needled superabsorbent composite material as a liquid management material. FIG. 15 merely shows the relationship between the layers of the exemplary absorbent structure, and is not intended to limit in any way the various ways those layers (or other layers) may be configured in particular products. The exemplary absorbent structure 100, shown here as a multi-layer composite suitable for use in a disposable diaper, feminine pad or other personal care product, contains four layers: a top layer 102, a liquid management layer 104, an optional absorbent layer 106, and a bottom layer 108. The top layer 102 may be a nonwoven web of melt-spun fibers or filaments, an apertured film or an embossed netting. The top layer 102 may function as a liner for a disposable diaper, or a cover layer for a feminine care pad or personal care product. The upper surface 110 of the top layer 102 is the portion of the absorbent structure 100 intended to contact the skin of a wearer. The lower surface 112 of the top layer 102 is superposed on the liquid management layer 104 which is one or more layers of a hydraulically needled superabsorbent composite material of the present invention. The liquid management layer 104 serves to rapidly desorb liquid from the top layer 102, distribute liquid throughout the liquid management layer 104 and retain liquid. If an absorbent layer 106 is included in the structure 100, the liquid management layer may also release liquid to the absorbent layer 106. The liquid management layer has an upper surface 114 in contact with the lower surface 112 of the top layer 102. The liquid management layer 104 also has a lower surface 116 superposed on the upper surface 118 of the optional absorbent layer 106. The liquid management layer 104 may have a different size or shape from the optional absorbent layer 106. The absorbent layer 106 may be layer of pulp fluff, superabsorbent material, or mixtures of the same. If present, the absorbent layer 106 is superposed over a fluid-impervious bottom layer 108. The absorbent layer 106 would have a lower surface 120 which is in contact with an upper surface 122 of the fluid impervious layer 108. The bottom surface 124 of the fluid-impervious layer 108 provides the outer surface for the absorbent structure 100. In more conventional terms, the liner layer 102 is a topsheet, the fluid-impervious bottom layer 108 is a backsheet, the liquid management layer 104 is a liquid distribution and retention layer, and the optional absorbent layer 106 is an absorbent core. Each layer may be separately formed and joined to the other layers in any conventional manner. The layers may be cut or shaped before or after assembly to provide a particular absorbent personal care product configuration.

When the layers are assembled to form a product such as, for example, a disposable diaper, the liquid management layer 104 formed from one or more layers of the hydraulically needled superabsorbent composite material of the present invention provides the advantages of reducing liquid retention in the top layer, improving liquid transport away from the skin, and more efficient use of the optional absorbent layer 106 by distributing liquid to a greater portion of the absorbent. These advantages are provided by improved vertical wicking and liquid absorption properties.

As noted above, other absorbent structures are contemplated. For example, an absorbent structure may contain a liner layer, a liquid surge layer (e.g., a resilient bonded, carded web), one or more layers of the hydraulically needled superabsorbent composite material of the present invention, an optional absorbent core or pulp fluff layer and a fluid-impervious bottom layer. In some applications, it may be desirable to have a liner layer, a pulp fluff layer, one or more layers of the hydraulically needled superabsorbent composite material of the present invention, and a fluid-impervious bottom layer.

One or more layers of the hydraulically needled superabsorbent composite material may be used as a liquid management material for many products besides disposable personal care products. For example, the absorbent nonwoven composite material may be used as a liquid management material in food and product packaging, wipers, wound dressings, industrial sorbents, and kennel and catbox liners.

EXAMPLES

Examples 1-6 illustrate exemplary hydraulically needled superabsorbent composite materials and various components of the composite materials.

EXAMPLE 1

A mixture of about 30% by weight uncrimped rayon fibers (about 1.5 denier, length about 19 mm), about 49% by weight LL19 Northern softwood unrefined kraft virgin wood fiber pulp (Longlac 19 available from the Kimberly-Clark Corporation) and about 21% by weight LL16 Northern hardwood kraft virgin wood fiber pulp (Longlac 16 available from the Kimberly-Clark Corporation) was wet-laid utilizing conventional papermaking techniques. The wet-laid web was dewatered to a consistency of approximately 25 percent solids and was hydraulically needled on a semi-twill stainless steel wire fabric having a mesh of 55 (number of filaments per inch running in the machine direction) and a count of 38 (number of filaments per inch running in the cross-machine direction) available from National Wire Fabric of Star City, Ark. The web was needled with columnar jets of water at about 300 psig from 2 manifolds each equipped with a jet strip having 0.007 inch diameter holes (1 row of holes at a density of 30 holes per inch). The discharge of the jet orifices were between about 2 cm to about 3 cm above the wet-laid web which travelled at a rate of about 80 feet per minute. Vacuum boxes removed excess water and the treated web was dried utilizing a rotary through-air dryer manufactured by Honeycomb Systems Incorporated of Biddeford, Me.

Portions of the wet-laid fibrous web described above were hydraulically needled at pressures of 500 and 800 psig and then through-air dried to provide examples of greater needling energies on the fibrous web. Other portions of the wet-laid fibrous web were not hydraulically needled. Instead, that material was through-air dried and kept as a control material.

Liquid distribution and retention properties for the hydraulically needled and control materials were measured and are reported in Table I.

EXAMPLE 2

The procedure of Example 1 was repeated except that the fibrous web was formed so it would have a basis weight of about 70 grams per square meter. Superabsorbent particles were added to the fibrous web just after hydraulic needling and before the web reached the vacuum boxes. The superabsorbent particles were sodium polyacrylate particles available from the Hoechst Celanese Corporation under the trade name Sanwet IM-5000 P. The particles were deposited onto the hydraulically needled web utilizing a gravity-drop type particulate spreader (Scotts PF Spreader) at a rate which produced a composite having a basis weight (when substantially dry) of about 100 grams per square meter. Thus, the substantially dry composite contained about 34% by weight LL19 wood pulp, 15% by weight LL16 wood pulp, 30% by weight superabsorbent and 21% by weight rayon staple fibers.

Vacuum boxes removed excess water and the composite material was dried utilizing a rotary through-air dryer. Liquid distribution and retention properties for the material were measured and are reported in Table I. Hydraulically needled superabsorbent composite materials of this example have the same basis weight as the hydraulically needled fibrous webs of Example 1. The wicking height appears to be only slightly decreased by the addition of superabsorbent and the wicking pickup and saturation capacity are significantly increased.

EXAMPLE 3

A nonwoven fibrous web of Northern softwood kraft unrefined virgin wood fiber pulp (Longlac 19 available from the Kimberly-Clark Corporation) was wet-laid utilizing conventional papermaking techniques. The wet-laid web was de-watered to a consistency of approximately 25 percent solids and was hydraulically needled on a conventional 100×92 mesh stainless steel semi-twill fabric available from National Wire Fabric of Star City, Ark. The web was needled with columnar jets of water at about 50 psig from 3 manifolds each equipped with a jet strip having 0.007 inch diameter holes (1 row of holes at a density of 30 holes per inch). The discharge of the jet orifices were between about 2 cm to about 3 cm above the wet-laid web which travelled at a rate of about 21 feet per minute. Vacuum boxes removed excess water and the treated web was dried utilizing a rotary through-air dryer manufactured by Honeycomb Systems Incorporated of Biddeford, Me.

Portions of the wet-laid fibrous web described above were hydraulically needled at pressures of 100, 200, 300 and 400 psig and then through-air dried to provide examples of greater needling energies on the fibrous web. Other portions of the wet-laid fibrous web were not hydraulically needled. Instead, that material was through-air dried and kept as a control material.

Liquid distribution and retention properties for the hydraulically needled and control materials were measured and are reported in Table I.

EXAMPLE 4A

The procedure of Example 3 was repeated except that the fibrous web was formed so it would have a basis weight of about 105 grams per square meter. Sanwet IM-5000 P superabsorbent material was added to the fibrous web just after hydraulic needling and before the web reached the vacuum boxes utilizing a gravity-drop type particulate spreader (Scotts PF Spreader). The superabsorbent was deposited at a rate which produced a composite having a basis weight (when substantially dry) of about 150 grams per square meter. Thus, the substantially dry composite contained about 70% by weight LL19 wood pulp and about 30% by weight superabsorbent.

Vacuum boxes removed excess water and the composite material was dried utilizing a rotary through-air dryer. Liquid distribution and retention properties for the material were measured and are reported in Table I. Hydraulically needled superabsorbent composite materials of this example contain a fibrous web having about the same basis weight as the hydraulically needled fibrous webs of Example 3. The wicking height appears to be only slightly decreased by the addition of superabsorbent and the wicking pickup and saturation capacity are significantly increased.

EXAMPLE 4B

The procedure of Example 4A was repeated except that the fibrous web was formed so it would have a basis weight of about 75 grams per square meter. Because the basis weight of the web was about 30 grams per square meter less than the web of Example 4A, the web passed under the hydraulic needling manifolds at a greater speed (about 28 feet per minute) to decrease the amount of energy transferred from the fluid jets to the lower basis weight web. Sanwet IM-5000 P superabsorbent material was added to the fibrous web just after hydraulic needling and before the web reached the vacuum boxes as described in Example 4A. The superabsorbent was deposited at a rate which produced a composite having a basis weight (when substantially dry) of about 150 grams per square meter. Thus, the substantially dry composite contained about 50% by weight LL19 wood pulp and about 50% by weight superabsorbent.

Vacuum boxes removed excess water and the composite material was dried utilizing a rotary through-air dryer. Liquid distribution and retention properties for the material were measured and are reported in Table I. Hydraulically needled superabsorbent composite materials of this example contain a fibrous web having about the same basis weight as the hydraulically needled fibrous webs of Example 3. The wicking height appears to be only slightly decreased by the addition of superabsorbent and the wicking pickup and saturation capacity is significantly increased.

Example 4C

The procedure of Example 4A was repeated except that the fibrous web was formed so it would have a basis weight of about 50 grams per square meter. Because the basis weight of the web was about 55 grams per square meter less than the web of Example 4A, the web passed under the hydraulic needling manifolds at a greater speed (about 40 feet per minute) to decrease the amount of energy transferred from the fluid jets to the lower basis weight fibrous web. Sanwet IM-5000 P superabsorbent material was added to the fibrous web just after hydraulic needling and before the web reached the vacuum boxes as described in Example 4A. The superabsorbent was deposited at a rate which produced a composite having a basis weight (when substantially dry) of about 125 grams per square meter. Thus, the substantially dry composite contained about 40% by weight LL19 wood pulp and about 60% by weight superabsorbent.

Vacuum boxes removed excess water and the composite material was dried utilizing a rotary through-air dryer. Liquid distribution and retention properties for the material were measured and are reported in Table I. The hydraulically needled superabsorbent composite material of this example contains a relatively large proportion of superabsorbent particles, yet it still provides a desirable vertical wicking height and excellent wicking pickup.

EXAMPLE 5

The procedure of Example 3 was repeated and the wet-laid web was de-watered to a consistency of approximately 25 percent solids. The web was hydraulically needled on a conventional 100 × 92 mesh stainless steel semi-twill forming fabric available from National Wire Fabric of Star City, Ark. The needling was carried out with columnar jets of water at about 200 psig from 3 manifolds each equipped with a jet strip having 0.007 inch diameter holes (1 row of holes at a density of 30 holes per inch). The discharge of the jet orifices were between about 2 cm to about 3 cm above the wet-laid web which travelled at a rate of about 50 feet per minute. Vacuum boxes removed excess water and the treated web was dried utilizing a rotary through-air dryer manufactured by Honeycomb Systems Incorporated of Biddeford, Me.

Portions of the wet-laid fibrous web described above were not hydraulically needled. Instead, that material was through-air dried and kept as a control material.

Liquid distribution and retention properties for the hydraulically needled and control materials were measured and are reported in Table I. This example shows how hydraulically needling a pulp fiber web improves its vertical wicking height, vertical wicking pickup and saturation capacity.

EXAMPLE 6A

The procedure of Example 5 was repeated except that Sanwet IM-5000 P superabsorbent material was added to the fibrous web just after hydraulic needling and before the web reached the vacuum boxes as described in Example 4A. The superabsorbent was added at a rate which produced a composite having a basis weight (when substantially dry) of about 150 grams per square meter. Thus, the substantially dry composite contained about 50% by weight LL19 wood pulp and about 50% by weight superabsorbent.

Vacuum boxes removed excess water and the composite material was dried utilizing a rotary through-air dryer. Liquid distribution and retention properties for the material were measured and are reported in Table I. The superabsorbent composite material of this example contains a hydraulically needled fibrous web having about same basis weight as the fibrous webs of Example 5. The wicking height appears to be only slightly decreased by the addition of superabsorbent and the wicking pickup is increased.

EXAMPLE 6B

The procedure of Example 6A was followed except that Sanwet IM-5000 P superabsorbent material was added to an identical wet-laid fibrous web which was not hydraulically needled. The superabsorbent was added at a rate which produced a composite having a basis weight (when substantially dry) of about 185 grams per square meter. Thus, the substantially dry composite contained about 40% by weight LL19 wood pulp and about 60% by weight superabsorbent.

Vacuum boxes removed excess water and the composite material was dried utilizing a rotary through-air dryer. Liquid distribution and retention properties for the material were measured and are reported in Table I. The superabsorbent composite material of this example contains an un-needled fibrous web having about same basis weight as the fibrous webs of Example 5. The result of the vertical wicking height test is reduced by the addition of superabsorbent and is less than the value measured for the hydraulically needled composite of Example 6A. The saturation capacity measured for the material of the present example is greater than that for its hydraulically needled counterpart. This is believed to be due to the greater loading of superabsorbent particles in the present example.

EXAMPLE 7

This example provides a comparison of a hydraulically needled superabsorbent composite material according to Example 4B and a commercial superabsorbent/tissue composite available under the trade designation Gelok from the Gelok International Corporation of Dunbridge, Ohio. Gelok is a laminate which includes 2 layers of tissue (each about 45 grams per square meter) sandwiching a layer of superabsorbent particles (about 75 grams per square meter) lightly bonded to the tissue for a total basis weight of about 165 grams per square meter. About 45% by weight of this material is superabsorbent.

Liquid distribution and retention properties for the Gelok tissue layer, and the Gelok laminate were measured. A comparison of these materials with the hydraulically needled superabsorbent composite material of Example 4B is given in Table II. As can been seen from Table II, the hydraulically needled superabsorbent composite material has better liquid distribution and retention properties as seen from its performance in the vertical wicking height and pickup test results.

EXAMPLE 8

This example provides a comparison of a high basis weight laminate of hydraulically needled superabsorbent composite materials with conventional pulp fluff/superabsorbent composites commonly used in disposable personal care products such as, for example, diapers.

Four layers of the hydraulically needled superabsorbent composite material of Example 4C were superposed into a multi-layer structure. The basis weight of the multi-layer structure was about 540 grams per square meter, slightly higher than expected but attributable to variability in basis weight of the individual layers.

The fluff/superabsorbent composites were formed utilizing conventional air-laying equipment and techniques to deposit a mixture of Southern softwood wood pulp fluff (Coosa River pulp fluff #54) available from the Kimberly-Clark Corporation and IM-5000 P superabsorbent. One air-formed composite had a basis weight of about 654 grams per square meter and contained about 50% by weight superabsorbent. A second air-formed composite had a basis weight of about 830 grams per square meter and contained about 12% by weight superabsorbent.

Liquid distribution and retention properties for the materials were measured and are reported in Table III. As can been seen from Table III, the hydraulically needled superabsorbent composite material has better liquid distribution properties as measured by the vertical wicking height test. Despite the differences in basis weight, the wicking pickup values for each material were about the same. When the wicking pickup values were normalized (assuming a linear relationship between pickup and basis weight) to a basis weight of 600 grams per square meter, it can be seen that the hydraulically needled superabsorbent composite material provided superior wicking pickup values.

TABLE I

| Example | Furnish | Line Speed (ft/min) | Basis Weight (gsm) | Needling Pressure (psig) | Vertical Height (cm) | Wicking Pickup (g) | Saturation Capacity (%) |
|---|---|---|---|---|---|---|---|
| 1A | 30% Rayon 70% Pulp | 80 | 100 | 0 | 17.5 | 5.9 | 555 |
| 1B | 30% Rayon 70% Pulp | 80 | 100 | 300 | 27.5 | 11.1 | 687 |
| 1C | 30% Rayon 70% Pulp | 80 | 100 | 500 | 26.5 | 10.3 | 745 |
| 1D | 30% Rayon 70% Pulp | 80 | 100 | 800 | 26.2 | 10.0 | 795 |
| 2 | 30% SAM/ 21% Rayon 49% Pulp | 80 | 100 | 550 | 17.0 | 19.0 | 1162 |
| 3A | 100%LL19 | 21 | 100 | 0 | 20.0 | 5.7 | 486 |
| 3B | 100%LL19 | 21 | 100 | 50 | 21.5 | 6.0 | |
| 3C | 100%LL19 | 21 | 100 | 100 | 23.5 | 7.9 | |
| 3D | 100%LL19 | 21 | 100 | 200 | 23.5 | 8.0 | 656 |
| 3E | 100%LL19 | 21 | 100 | 300 | 23.0 | 7.3 | |
| 3F | 100%LL19 | 21 | 100 | 400 | 21.0 | 6.3 | 668 |
| 4A | 30% SAM | 21 | 150 | 200 | 17.0 | 21.7 | 1350 |
| 4B | 50% SAM | 28 | 150 | 200 | 18.5 | 22.5 | 1680 |
| 4C | 60% SAM | 40 | 125 | 200 | 16.3 | 23.5 | |
| 5A | 100%LL19 | 25 | 78 | 0 | 21.0 | 4.7 | 590 |
| 5B | 100%LL19 | 25 | 78 | 200 | 24.0 | 8.7 | 813 |
| 6A | 60% SAM | 25 | 185 | 0 | 15.0 | 23.5 | 1650 |
| 6B | 50% SAM | 25 | 150 | 200 | 17.0 | 26.7 | 1580 |

TABLE II

| Example | Furnish | Basis Weight (gsm) | Vertical Wicking Height (cm) | Pickup (g) |
|---|---|---|---|---|
| 7 | Gelok Tissue | 45 | 6.3 | 2.2 |
| 7 | Gelok 45% SAM | 165 | 8.3 | 14.7 |
| 7 | mat'l from Example 4B | 150 | 15.3 | 23.5 |

TABLE III

| Example | Furnish | Basis Weight (gsm) | Vertical Wicking Height (cm) | Pickup (g) | Pickup @ 600 gsm |
|---|---|---|---|---|---|
| 8 | Fluff/SAM (50%) | 654 | 6 | 105 | 96 |
| 8 | Fluff/Sam (12%) | 830 | 14 | 109 | 80 |
| 8 | 4 layers mat'l | 540 | 15.5 | 111 | 123 |

TABLE III-continued

| Example | Furnish | Basis Weight (gsm) | Vertical Wicking Height (cm) | Pickup (g) | Pickup @ 600 gsm |
|---|---|---|---|---|---|
| | from Example 4C | | | | |

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A process of making a hydraulically needled superabsorbent composite material, said process comprising the steps of:
    providing a nonwoven fibrous web;
    hydraulically needling the nonwoven web so that its vertical wicking properties are adapted to be at least about 10 percent greater than an identical nonwoven web which has not been hydraulically needled; and
    introducing dry superabsorbent materials into intimate bonding contact with at least one surface of said hydraulically needled nonwoven fibrous web to form a hydraulically needled superabsorbent composite material.

2. The process of claim 1 wherein dry superabsorbent materials are introduced onto at least one surface of the hydraulically needled nonwoven fibrous web while said web is wet and then the hydraulically needled nonwoven fibrous web and superabsorbent materials are dried to produce the superabsorbent composite material.

3. The process of claim 1 wherein dry superabsorbent materials are deposited onto at least one surface of a substantially dry hydraulically needled nonwoven fibrous web and then introduced into intimate bonding contact with said web by applying pressure to drive the superabsorbent materials into the hydraulically needled nonwoven fibrous web to produce the superabsorbent composite material.

4. The process of claim 1 wherein the nonwoven fibrous web is provided by depositing an aqueous suspension comprising fibers onto a foraminous surface.

5. The process of claim 1 wherein the nonwoven fibrous web is provided by rehydrating a sheet comprising pulp fibers.

6. The process of claim 1 wherein the nonwoven fibrous web is hydraulically needled at a consistency ranging from about 15 to about 35 percent, by weight, solids.

7. The process of claim 1 wherein the hydraulic needling is at an energy level of about 0.03 to about 0.001 horsepower-hours/pound of dry fibers.

8. The process of claim 4 wherein the foraminous surface is selected from the group consisting of single plane mesh having a mesh size of from about 20×20 to about 200×200, multi-ply meshes having an effective mesh size of from about 20×20 to about 200×200, and perforated plates.

9. The process of claim 4 wherein the said fibers are selected from the group consisting of pulp fibers, synthetic fibers, natural fibers, bicomponent fibers, continuous filaments and mixtures thereof.

10. The process of claim 6 wherein the nonwoven fibrous web is hydraulically needles while at a consistency ranging from about 20 to about 30 percent, by weight, solids.

11. The process of claim 1 wherein superabsorbent materials are deposited on the hydraulically needled nonwoven fibrous web in an amount which provides an absorbent nonwoven composite material containing at least about 5 percent, by weight, superabsorbent materials.

12. The process of claim 11 wherein superabsorbent materials are deposited on the hydraulically needled nonwoven fibrous web in an amount which provides an absorbent nonwoven composite material containing from about 10 to about 80 percent, by weight, superabsorbent material.

13. The process of claim 11 wherein superabsorbent particles are deposited on the hydraulically needled nonwoven fibrous web in an amount which provides an absorbent nonwoven composite material containing from about 30 to about 60 percent, by weight, superabsorbent material.

14. The process of claim 1 wherein the drying step utilizes a process selected from the group consisting of through-air-drying, infra red radiation, yankee dryers, drying cans, microwaves, and ultrasonic energy.

15. The process of claim 1 further comprising a mechanical softening step after the drying step.

16. A hydraulically needled superabsorbent nonwoven composite material produced by the process of claim 1, said nonwoven composite material comprising:
a nonwoven fibrous web which has been hydraulically needled so that its vertical wicking properties are adapted to be at least about 10 percent greater than an identical nonwoven web which has not been hydraulically needled; and
superabsorbent materials joined in intimate bonding contact to at least one surface of said hydraulically needled nonwoven fibrous web.

17. The superabsorbent nonwoven composite material of claim 16 having a basis weight greater than about 10 grams per square meter.

18. The superabsorbent nonwoven composite material of claim 16 having a basis weight from about 25 to about 400 grams per square meter.

19. The superabsorbent nonwoven composite material of claim 16 wherein the nonwoven fibrous web comprises from about 5 to about 50 percent, by weight, staple length fibers selected from the group consisting of polyester fibers, rayon fibers, cotton fibers, polyamide fibers, acrylic fibers, and polyolefin fibers.

20. The superabsorbent nonwoven composite material of claim 18 having a basis weight from about 75 to about 150 grams per square meter.

21. The superabsorbent nonwoven composite material of claim 16 having a saturation capacity greater than about 500 percent and a vertical wicking rate greater than about 12 cm per 15 minutes.

22. The superabsorbent nonwoven composite material of claim 21 having a saturation capacity from about 600 to about 2500 percent.

23. The superabsorbent nonwoven composite material of claim 21 having a wicking rate from about 12 to about 15 cm per 15 minutes.

24. The superabsorbent nonwoven composite material of claim 16 wherein the material contains from about 5 to about 80 percent, by weight, of superabsorbent materials.

25. The superabsorbent nonwoven composite material of claim 24 wherein the material contains from about 10 percent to about 65 percent, by weight, of superabsorbent materials.

26. A liquid management component of an absorbent product, said component comprising at least one layer of the superabsorbent nonwoven composite material of claim 16.

27. An absorbent structure including a liquid management component comprising at least one layer of the superabsorbent nonwoven composite material of claim 16.

* * * * *

UNITED STATES PATENT AND TRADEMARK OFFICE
CERTIFICATE OF CORRECTION

PATENT NO. : 5,328,759
DATED : July 12, 1994
INVENTOR(S) : Ann L. McCormack; Fred R. Radwanski; Cherie H. Everhart It is certified that error appears in the above-indentified patent and that said Letters Patent is hereby corrected as shown below:

Column 7, line 13, "and 35 abrasion resistance" should read --and abrasion resistance--;

Column 16, line 64, "Example 4C" should read --EXAMPLE 4C--.

Signed and Sealed this

Thirteenth Day of February, 1996

*Attest:*

BRUCE LEHMAN

*Attesting Officer*   *Commissioner of Patents and Trademarks*